(12) United States Patent
Kamimura et al.

(10) Patent No.: US 9,492,494 B2
(45) Date of Patent: Nov. 15, 2016

(54) ORAL COMPOSITION

(75) Inventors: Ayako Kamimura, Tokyo (JP); Yasushi Sakai, Tsukuba (JP); Takeshi Ikeda, Tsukuba (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 301 days.

(21) Appl. No.: 12/602,597

(22) PCT Filed: May 30, 2008

(86) PCT No.: PCT/JP2008/059994
§ 371 (c)(1),
(2), (4) Date: Dec. 1, 2009

(87) PCT Pub. No.: WO2008/146907
PCT Pub. Date: Dec. 4, 2008

(65) Prior Publication Data
US 2010/0249028 A1 Sep. 30, 2010

(30) Foreign Application Priority Data
Jun. 1, 2007 (JP) ................................. 2007-147537

(51) Int. Cl.
| A61K 38/00 | (2006.01) |
| --- | --- |
| C07K 16/00 | (2006.01) |
| A61K 38/01 | (2006.01) |
| A23L 1/305 | (2006.01) |
| A23L 2/52 | (2006.01) |
| A23L 2/66 | (2006.01) |
| A61K 31/401 | (2006.01) |
| A61K 38/39 | (2006.01) |

(52) U.S. Cl.
CPC .............. *A61K 38/014* (2013.01); *A23L 1/305* (2013.01); *A23L 1/3051* (2013.01); *A23L 1/3053* (2013.01); *A23L 2/52* (2013.01); *A23L 2/66* (2013.01); *A61K 31/401* (2013.01); *A61K 38/39* (2013.01); *A23V 2002/00* (2013.01)

(58) Field of Classification Search
CPC .. A61K 9/0014; A61K 47/42; A61K 31/045; C07K 14/78
See application file for complete search history.

(56) References Cited

U.S. PATENT DOCUMENTS

| 3,932,638 | A | * | 1/1976 | Coirre et al. ................. 514/184 |
| --- | --- | --- | --- | --- |
| 4,130,555 | A | * | 12/1978 | Ohtsuka et al. .............. 530/354 |
| 5,215,756 | A | | 6/1993 | Gole et al. |
| 5,330,763 | A | | 7/1994 | Gole et al. |
| 5,330,764 | A | | 7/1994 | Gole et al. |
| 5,558,880 | A | | 9/1996 | Gole et al. |
| 5,648,093 | A | | 7/1997 | Gole et al. |
| 6,692,754 | B1 | | 2/2004 | Makimoto et al. |
| 7,091,180 | B2 | * | 8/2006 | Ishaq ........................... 514/17.1 |
| 2002/0119950 | A1 | | 8/2002 | Henderson et al. |
| 2003/0129261 | A1 | | 7/2003 | Henderson et al. |
| 2004/0197431 | A1 | | 10/2004 | Henderson et al. |
| 2006/0035957 | A1 | | 2/2006 | Takeda et al. |
| 2006/0264498 | A1 | * | 11/2006 | Kamiya et al. ................ 514/423 |
| 2007/0141181 | A1 | | 6/2007 | Henderson et al. |
| 2007/0293427 | A1 | | 12/2007 | Vouland et al. |
| 2009/0062371 | A1 | | 3/2009 | Kamiya et al. |
| 2009/0087503 | A1 | | 4/2009 | Henderson et al. |
| 2009/0254104 | A1 | | 10/2009 | Murray |
| 2010/0105632 | A1 | | 4/2010 | Henderson et al. |

FOREIGN PATENT DOCUMENTS

| CA | 2327882 A | 10/1999 |
| --- | --- | --- |
| CN | 1304416 A | 7/2001 |
| CN | 1684679 A | 10/2005 |
| EP | 1612206 A1 | 1/2006 |
| EP | 1 795 191 A1 | 6/2007 |
| JP | H07-508019 A | 9/1995 |
| JP | 07-278012 A1 | 10/1995 |
| JP | 2000-201649 A1 | 7/2000 |
| JP | 2001-131084 A1 | 5/2001 |
| JP | 2001-224334 A1 | 8/2001 |
| JP | 2002-516829 A1 | 6/2002 |
| JP | 2003-137807 A1 | 5/2003 |
| JP | 2004-238386 A1 | 8/2004 |
| JP | 2005-119983 A1 | 5/2005 |
| JP | 2005-145929 A1 | 6/2005 |
| TW | I224010 B | 11/2004 |
| WO | WO 99/24046 A1 | 5/1999 |
| WO | WO 99/62459 A2 | 12/1999 |
| WO | WO 2004/087657 A1 | 10/2004 |
| WO | WO 2006/033355 A1 | 3/2006 |
| WO | WO 2007/111238 A1 | 10/2007 |
| WO | WO 2007/122179 A1 | 11/2007 |
| WO | WO 2008/060361 A2 | 5/2008 |

OTHER PUBLICATIONS

J. E. Eastoe The British Gelatin and Glue Research Association, vol. 16, Apr. 1955.*
"Biochemical Data Book I," The Japanese Biochemical Society (1981), pp. 1667-1668.
"Karei to Hihu (Aging and Skin)," Seishi Shoin (1986), pp. 33-36.
"Mechanism and Control of Aging," IPC (1993), pp. 151-152.
"Seikagaku Jiten (Biomedical Dictionary)," first edition, Tokyo Kagaku Dojin (1984), p. 480.
European Patent Office, Supplementary European Search Report issued in European Patent Application No. 08 76 4912 (Dec. 21, 2012).

(Continued)

*Primary Examiner* — Jeanette Lieb
(74) *Attorney, Agent, or Firm* — Leydig, Voit & Mayer, Ltd.

(57) ABSTRACT

An object of the present invention is to provide an oral composition useful for promoting collagen synthesis and the like. The present invention can provide an oral composition containing collagen or gelatin or a degradation product thereof, and hydroxyproline or a salt thereof. The weight ratio of alanine and hydroxyproline contained in the amino acids obtained by hydrolyzing the oral composition is preferably 1:1.5-150.

6 Claims, No Drawings

(56) References Cited

OTHER PUBLICATIONS

Kikuchi et al., *Fragrance Journal*, 9: 97-102 (2003).
Ueno et al., *Oyo Yakuri Pharmacometrics*, 73(1/2): 183-190 (2007).

The State Intellectual Property Office of the People's Republic of China, Notification of the Fourth Office Action in Chinese Patent Application 200880100419.7 (Jan. 15, 2014).
Japanese Patent Office, Office Action in Japanese Patent Application No. 2009-516367 (May 28, 2013).

* cited by examiner

ORAL COMPOSITION

TECHNICAL FIELD

The present invention relates to an oral composition comprising collagen or gelatin or a degradation product thereof, and hydroxyproline or a salt thereof.

BACKGROUND ART

Collagen is a main protein component of extracellular matrix filling the gap between cells or between cell populations of biological tissues, and is said to sometimes make up nearly 30% of the total protein of the body in mammals (see non-patent document 1).

Collagen forms fibrous or membrane structures, has a primary function of maintenance, support, connection, reinforcement and the like of tissue structures, and is present in the skin, bone, tendon, ligament, cornea, blood vessel and the like in large amounts. Decrease, denaturation and the like of tissue collagen are considered to be the major factors causing wrinkles, sagging, osteoporosis and the like, which are developed by aging of these tissues. In fact, reports have also documented that tissue collagen decrease strikingly by exposure to sun light for a long time (see non-patent document 2), and that age-related low metabolism of biogenic substances advances as triggered by low collagen metabolism (see non-patent document 3).

In addition, it is known that the weight ratio of alanine and hydroxyproline from among the amino acids constituting collagen or gelatin is 1:1.3 (see non-patent document 4).

As a method for enhancing collagen metabolism, a collagen synthesis promoting action by collagen degradation product is known (see patent documents 1-4).

In addition, hydroxyproline is known to have a collagen synthesis promoting action on cultured human fibroblasts, and a wrinkle formation suppressive or improving effect by topical application (see patent document 5).

Furthermore, amino acid-containing cosmetics which contain collagen-constituent amino acids such as glycine, proline, alanine and the like (see patent document 6), and such cosmetics containing hydroxyproline (see patent document 7) are known.

However, it is considered that the effect of collagen-containing foods or drinks is hardly felt unless it is ingested in the order of several grams, and also, the smell or taste in some ingestion form prevents easy ingestion. In view of such problems, a new method capable of decreasing the ingestion amount of collagen has been desired.

Moreover, a combination effect of collagen or gelatin or a degradation product thereof, and hydroxyproline is not known.

non-patent document 1: "Seikagaku Jiten (Biochemical Dictionary) first edition", Tokyo Kagaku Dojin, 1984, p. 480
non-patent document 2: "Karei to Hihu (Aging and Skin)", Seishi Shoin, 1986, p. 35
non-patent document 3: "Mechanism and Control of Aging", IPC, 1993, p. 151
non-patent document 4: "Biochemical Data Book I", The Japanese Biochemical Society, 1981, p. 1667
patent document 1: JP-A-7-278012
patent document 2: JP-A-2000-201649
patent document 3: JP-A-2001-131084
patent document 4: JP-A-2003-137807
patent document 5: JP-A-7-278012
patent document 6: JP-A-2001-224334
patent document 7: JP-A-2006-79921

DISCLOSURE OF THE INVENTION

Problems to be Solved by the Invention

An object of the present invention is to provide an oral composition comprising collagen or gelatin or a degradation product thereof, and hydroxyproline or a salt thereof.

Means of Solving the Problems

The present invention relates to the following (1)-(5).
(1) An oral composition comprising a composition of collagen or gelatin or a degradation product thereof, and hydroxyproline or a salt thereof.
(2) An oral composition comprising a composition of collagen or gelatin or a degradation product thereof, and hydroxyproline, wherein the weight ratio of alanine and hydroxyproline contained in the amino acid obtained by hydrolyzing the oral composition is 1:1.5-150.
(3) An oral composition comprising a composition of collagen or gelatin or a degradation product thereof, and hydroxyproline or a salt thereof, wherein the weight ratio of alanine and hydroxyproline contained in the amino acid obtained by hydrolyzing the oral composition is 1:1.5-150.
(4) A method of producing an oral composition comprising adding hydroxyproline to a composition comprising collagen or gelatin or a degradation product thereof.
(5) The production method of (4) above, wherein hydroxyproline is added such that the weight ratio of alanine and hydroxyproline contained in the amino acids obtained by hydrolyzing the oral composition is 1:1.5-150.

Effect of the Invention

The present invention can provide an oral composition comprising collagen or gelatin or a degradation product thereof, and hydroxyproline or a salt thereof. The oral composition can be used as a collagen synthesis promoter, an agent for reducing dryness of the face, and the like.

BEST MODE FOR CARRYING OUT THE INVENTION

The collagen or gelatin to be used for the present invention may be any as long as it is derived from animals, such as those derived from domestic animals (pig, cow, chicken etc.), those derived from fish, shellfish and the like.

As the collagen, commercially available products such as collagen P and Maringen S-06 (PF) (which are manufactured by Nitta Gelatin Inc.) and the like can also be used. As the gelatin, commercially available products such as fish gelatin (IXOS series), pig-derived gelatin (APH series) (which are manufactured by Nitta Gelatin Inc.) and the like can also be used.

The degradation product of collagen or gelatin may be one obtained with hydrolytic enzymes, or hydrolysis with acid or alkali.

Examples of the hydrolytic enzyme include neutral protease, alkaline protease, acidic protease and the like. As the hydrolytic enzyme, commercially available products such as "protease p-3" (manufactured by Amano Enzyme Inc., alkaline protease) and the like can also be used.

As the degradation product of collagen, commercially available products such as collagen peptide 800F, IXOS HDL series (which are manufactured by Nitta Gelatin Inc.) and the like can also be used. In addition, as the degradation product of gelatin, commercially available products such as water-soluble collagen peptide DS, water-soluble collagen peptide SS (which are sold by Kyowa Wellness Co., Ltd.) and the like can also be used.

The molecular weight of the collagen or gelatin or a degradation product thereof is generally 400-300,000, preferably 500-100,000, and those with 500-15,000 are preferably used.

The hydroxyproline to be used in the present invention includes 8 kinds of stereoisomers depending on whether proline of hydroxyproline is D form or L form, and whether the position of hydroxyl group is the 3-position or the 4-position, and whether the stereoisomer thereof is cis or trans.

Specific examples of hydroxyproline include cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline, with preference given to trans-4-hydroxy-L-proline.

Hydroxyproline is one kind of amino acid widely present in the natural world as a main constituent amino acid component in collagen or constituent amino acid of elastin. For example, it can be produced by hydrolyzing animal-derived collagen with an acid and purifying according to a conventional method.

trans-4-Hydroxy-L-proline can be produced by the use of proline 4-position hydroxygenase (JP-A-7-313179) isolated from the genus *Amycolatopsis* or *Dactylosporangium*. In addition, cis-4-hydroxy-L-proline can also be produced by the use of proline 3-position hydroxygenase (JP-A-7-322885) isolated from the genus *Streptomyces* (BIO INDUSTRY, vol. 14, No. 31, 1997).

Examples of the salt of hydroxyproline include acid addition salt, metal salt, ammonium salt, organic amine addition salt, amino acid addition salt and the like.

Examples of the acid addition salt include inorganic acid salts such as hydrochloride, sulfate, nitrate, phosphate and the like, organic acid salts such as acetate, maleate, fumarate, malate, lactate, α-ketoglutarate, gluconate, caprylate, orotic acid and the like.

Examples of the metal salt include alkali metal salts such as sodium salt, potassium salt and the like, alkaline earth metal salts such as magnesium salt, calcium salt and the like, aluminum salt, zinc salt and the like.

Examples of the ammonium salt include salts of ammonium, tetramethylammonium and the like.

Examples of the organic amine addition salt include salts with morpholine, piperidine and the like.

Examples of the amino acid addition salt include salts with glycine, phenylalanine, aspartic acid, glutamic acid and the like.

The weight ratio of alanine and hydroxyproline is not particularly limited when the amino acids are liberated by hydrolysis of the oral composition of the present invention. It is preferably 1:1.5-150, more preferably 1:2.5-100, particularly preferably 1:3.5-60.

As a method of hydrolyzing the oral composition, a method comprising adding 7 ml of 6-12M hydrochloric acid to 0.1 g of the oral composition and treating the mixture at 110° C. for 12 hr-24 hr, preferably 18 hr-24 hr, can be mentioned. When the oral composition is a solution such as drink and the like, the oral composition is preferably subjected to a treatment such as depressurization, heating and the like to give a dry solid product, which is then hydrolyzed.

The weights of alanine and hydroxyproline obtained by hydrolysis of the oral composition can be measured by, for example, hydrolyzing the oral composition according to the above-mentioned method to give a dry solid product under reduced pressure, dissolving the product in, for example, an eluent for full automatic amino acid, and applying the solution to a full automatic amino acid analyzer (manufactured by JEOL Ltd., JLC-500/V).

The content of the collagen or gelatin or a degradation product thereof and hydroxyproline in the oral composition of the present invention is such an amount as to set the proportion of hydroxyproline contained in free amino acids, which are liberated by hydrolysis of the oral composition, to preferably 0.001-95 wt %, more preferably 0.01-85 wt %, of the oral composition.

The oral composition of the present invention can be produced, for example, by adding hydroxyproline or a salt thereof to a composition containing collagen or gelatin or a m degradation product thereof such that, when amino acids are liberated by hydrolysis of the oral composition, the weight ratio of free alanine and hydroxyproline is 1:1.5-150, preferably 1:2.5-100, more preferably 1:3.5-60.

The oral composition of the present invention is also preferably used as a collagen synthesis promoter, face dryness reducing agent and the like. In this case, the oral composition preferably contains ascorbic acid or a derivative thereof or a salt thereof. The oral composition of the present invention preferably contains ascorbic acid or a derivative thereof or a salt thereof in a proportion of 0.0001 wt %-30 wt %, more preferably 0.001 wt %-10 wt %.

Ascorbic acid or a derivative thereof or a salt thereof may be any as long as it is pharmacologically acceptable. As an ascorbic acid derivative, for example, a phosphate ester form, sulfuric acid ester form and the like are used. As ascorbate, sodium salt, calcium salt and the like are used.

The oral composition of the present invention can be used, for example, as a medicament, food or drink or food additive (hereinafter also referred to as a medicament, food or drink, or food additive of the present invention).

When the oral composition of the present invention is used as a medicament, it is desirably provided generally as an oral preparation. The preparation can be produced by mixing with, in addition to the above-mentioned components, a carrier where necessary, and according to any method well known in the technical field of galenical pharmacy.

For formulation of the oral composition of the present invention into a preparation, additives such as excipient, binder, disintegrant, lubricant, dispersing agent, suspending agent, emulsifier, diluent, buffer, antioxidant, microbial inhibitor and the like can be used. As a dosage form of the preparation, tablet, powder, granule, emulsion, syrup, capsule and the like can be mentioned.

When the dosage form of the preparation is a liquid preparation such as syrup and the like, the preparation can be produced with the addition of water, saccharides such as saccharose, sorbitol, fructose and the like, glycols such as polyethylene glycol, propylene glycol and the like, oils such as sesame oil, olive oil, soybean oil and the like, preservatives such as p-hydroxybenzoic acid esters and the like, flavors such as strawberry flavor, peppermint and the like, and the like.

In the case of, for example, tablet, powder, granule and the like suitable for oral administration, moreover, the preparation can be produced with the addition of excipients such as saccharides (e.g., lactose, sucrose, glucose, saccharose, mannitol, sorbitol and the like), starch (e.g., potato, wheat, corn and the like), inorganic materials (e.g., calcium carbonate, calcium sulfate, sodium hydrogen carbonate, sodium chloride and the like), plant powder (e.g., *Glycyrrhiza uralensis, Gentiana lutea* powder and the like), and the like, disintegrants such as starch, agar, gelatin powder, crystalline cellulose, carmellose sodium, carmellose calcium, calcium carbonate, sodium hydrogen carbonate, sodium alginate and the like, lubricants such as magnesium stearate, talc, hydrogenated vegetable oil, macrogol, silicon oil and the like, binders such as polyvinyl alcohol, hydroxypropylcellulose, methylcellulose, ethylcellulose, carmellose, glue liquid and the like, surfactants such as fatty acid ester and the like, plasticizers such as glycerol and the like, and the like.

The dose of the oral composition of the present invention varies depending on the administration form, age and body weight of the person who receives administration and the like. As the weight of hydroxyproline liberated by hydrolysis of the oral composition, the daily dose for an adult is generally 0.1-5 g, preferably 0.1-2 g, more preferably 0.1-1 g, which is administered in one to several portions a day. While the dosing period is not particularly limited, it is generally one day to one year, preferably 1 week to 3 months.

The food additive of the present invention can be prepared by a method similar to that of the above-mentioned preparation. The food additive of the present invention is produced by mixing or dissolving other food additives as necessary and processing same into the form of, for example, powder, granule, pellet, tablet or various liquids.

The food or drink of the present invention can be processed and produced according to a general production method of food and drink, except that the food additive of the present invention is added.

The food or drink of the present invention can also be produced by, for example, a granulation method such as fluidized bed granulation, stirring granulation, extrusion-granulation, rolling granulation, stream granulation, compression molding granulation, lump-breaking granulation, spray granulation, injection granulation and the like, a coating method such as pan coating, fluidized bed coating, dry coating and the like, a swelling method such as puff drying, excess water vapor method, foam mat method, microwave heating method and the like, an extrusion method such as extrusion granulating machine, extruder and the like, and the like.

The food or drink of the present invention may be in any form and examples thereof include juice, soft drink, tea, milk products such as lactic acid bacteria beverage, fermented milk, frozen dessert, butter, cheese, yogurt, processed milk, skimmed milk and the like, meat products such as ham, sausage, hamburger and the like, fish processed seafood paste products such as fish cake, tube-like fish sausage, satumaage and the like, egg products such as Japanese omelets, steamed egg custard and the like, confectionery such as cookie, jelly, chewing gum, candy, snack and the like, bread, noodle, Japanese pickles, smoked food, dry food, food boiled in soy sauce, salt cured products, soup, seasoning and the like.

Moreover, the food or drink of the present invention may be in the form of, for example, powder food, sheet-like food, bottled food, canned food, retort food, capsule food, tablet-like food, liquid diet, health drink and the like.

The food and drink of the present invention can be used as food and drink for collagen synthesis promotion such as health food, functional food, supplements, food for specified health uses and the like.

The food and drink as well as food additive of the present invention may contain additives generally used for food and drink, for example, sweetener, colorant, preservative, thickeners and stabilizers, antioxidants, color developing agents, bleach, fungicide, gum base, bittering agent, enzyme, gloss agent, acidulant, seasoning, emulsifier, reinforcing agent, agents for production, flavor, spice extract and the like.

The oral composition of the present invention can be used not only for human but also animals other than human (hereinafter to be abbreviated as non-human animals).

Examples of the non-human animal include animals other than human such as mammals, birds, reptiles, amphibians, fish and the like.

The dose for administration to non-human animal varies depending on the age, kind and the like of the animal. As the weight of hydroxyproline liberated by hydrolysis of the oral composition, the daily dose per kg weight is generally 2-600 mg, preferably 2-360 mg, more preferably 2-180 mg, which is administered in one to several portions a day. While the dosing period is not particularly limited, it is generally one day to one year, preferably 1 week to 3 months.

Experimental Examples relating to the collagen synthesis promoting effect, face dryness reducing effect and sensory evaluation of the oral composition of the present invention are shown in the following.

Experimental Example 1

F344/DuCrlCrlj rats (male, 8-week-old, purchased from Charles River Laboratories Japan Inc.) were used. They were reared under an environment of temperature 23° C. and humidity 55%, using CE-2 (CLEA Japan, Inc.) as a feed with free access to drinking water. One group contained six rats, and the rats were grouped such that the body weights do not produce difference. The rats of each administration group were orally administered with the following composition or purified water as a sample liquid once a day for 12 consecutive days.

To be specific, the rats of the administration groups 1-5 were each administered with compositions 1-5 obtained by dissolving water-soluble collagen peptide SS (manufactured by Kyowa Hakko Kogyo Co., Ltd., hereinafter to be abbreviated as collagen peptide) and trans-4-hydroxy-L-proline (manufactured by Kyowa Hakko Kogyo Co., Ltd., hereinafter to be abbreviated as L-hydroxyproline) in purified water to the contents shown in Table 1 at 10 mL/kg. The rats of the control administration group 6 were administered with purified water at 10 mL/kg.

The contents of collagen peptide and L-hydroxyproline in each sample liquid, and the weight ratio of L-alanine and L-hydroxyproline in each sample liquid are shown in Table 1.

TABLE 1

| administration group | sample liquid | collagen peptide (g/L) | L-hydroxy-proline (g/L) | L-alanine: L-hydroxy-proline |
| --- | --- | --- | --- | --- |
| 1 | composition 1 | 10 | 50 | 1:58.84 |
| 2 | composition 2 | 50 | 50 | 1:12.86 |
| 3 | composition 3 | 10 | — | 1:1.37 |
| 4 | composition 4 | 50 | — | 1:1.37 |
| 5 | composition 5 | — | 50 | ∞ |
| 6 | purified water | — | — | — |

The weights of L-alanine and L-hydroxyproline contained in the amino acids obtained by hydrolyzing the compositions 1-5 were calculated as the weight of L-alanine contained in the amino acids obtained by hydrolyzing the collagen peptide contained in each composition, and a total amount of the weight of L-hydroxyproline contained in the amino acids and the weight of L-hydroxyproline contained in each composition, respectively. Of these, the weights of L-alanine and L-hydroxyproline contained in the amino acids obtained by hydrolyzing the collagen peptide were obtained by adding 12M hydrochloric acid (7 ml) to collagen peptide (100 mg), hydrolyzing the mixture at 110° C. for 18 hr and measuring the weights by a full automatic amino acid analyzer (manufactured by JEOL Ltd., JLC-500/V). As a result, collagen peptide (100 mg) contained 8.7 mg of L-alanine and 11.9 mg of L-hydroxyproline.

On the 13th day from the start of the administration test, the abdomen was shaved under anesthesia by intraperitoneal administration of pentobarbital, the abdominal skin was collected and, after frost shattering, soluble collagen was extracted with 0.45M sodium chloride. An equal amount of 6M hydrochloric acid was added to the extract, and the mixture was treated at 110° C. for 18 hr. The second amino group was labeled with NBD-Cl (4-chloro-7-nitro-2,1,3-benzoxadiazole, manufactured by Tokyo Chemical Industry Co., Ltd.) and the amount of L-hydroxyproline in the soluble collagen was analyzed by high performance liquid chromatography using an ODS column (4.6 cmφ×15 cm, manufactured by GL Sciences Inc.). The value is shown by mean±standard deviation, and the statistically significant difference test was performed by the student-t-test.

The results are shown in Table 2.

TABLE 2

| administration group | L-hydroxyproline amount/wet weight of skin (mg/g) | significant difference from administration group 6 |
| --- | --- | --- |
| 1 | 1.230 ± 0.072 | $p < 0.05$ |
| 2 | 1.352 ± 0.085 | $p < 0.05$ |
| 3 | 1.002 ± 0.156 | |
| 4 | 1.000 ± 0.105 | |
| 5 | 1.077 ± 0.215 | |
| 6 | 1.015 ± 0.183 | |

As shown in Table 2, the administration groups 3-5, to which a composition comprising collagen peptide or L-hydroxyproline alone was administered as a sample liquid, did not show an increase in the amount of L-hydroxyproline in the skin, i.e., the amount of soluble collagen. In contrast, the administration groups 1 and 2, to which a composition containing the collagen peptide and L-hydroxyproline was administered, showed a remarkable increase in the amount of soluble collagen.

Experimental Example 2

Using F344/DuCrlCrlj rats (male, 7-week-old, purchased from Charles River Laboratories Japan Inc.), an administration test similar to that in Experimental Example 1 was performed with 4 rats per group.

To the rats of the administration groups 7-11 were each administered with compositions 7-11 obtained by dissolving collagen peptide and L-hydroxyproline in purified water to the contents shown in Table 3 at 10 mL/kg. The rats of the control administration group 12 were administered with purified water at 10 mL/kg.

The contents of collagen peptide and L-hydroxyproline in each sample liquid, and the weight ratios of L-alanine and L-hydroxyproline in each test solution are shown in Table 3.

TABLE 3

| administration group | sample liquid | collagen peptide (g/L) | L-hydroxyproline (g/L) | L-alanine: L-hydroxyproline |
| --- | --- | --- | --- | --- |
| 7 | composition 7 | 50 | 10 | 1:3.67 |
| 8 | composition 8 | 50 | 30 | 1:8.26 |
| 9 | composition 9 | 50 | — | 1:1.37 |
| 10 | composition 10 | — | 10 | ∞ |
| 11 | composition 11 | — | 30 | ∞ |
| 12 | purified water | — | — | — |

The weights of L-alanine and L-hydroxyproline contained in the amino acids obtained by hydrolyzing the compositions 7-11 were calculated according to a method similar to that in Experimental Example 1.

On the 13th day from the start of the administration test, the abdomen was shaved under anesthesia by intraperitoneal administration of pentobarbital, and the abdominal skin was collected. The abdominal skin was treated with 6M hydrochloric acid at 110° C. for 18 hr, and the amounts of L-hydroxyproline in soluble collagen and insoluble collagen were measured according to a method similar to that in Experimental Example 1 and used as an index of collagen synthesizability. The values are shown by mean±standard deviation.

The results are shown in Table 4.

TABLE 4

| administration group | L-hydroxyproline amount/wet weight of skin (mg/g) |
| --- | --- |
| 7 | 12.39 ± 1.50 |
| 8 | 12.80 ± 2.37 |
| 9 | 9.91 ± 1.96 |
| 10 | 9.26 ± 1.70 |
| 11 | 10.66 ± 1.69 |
| 12 | 10.62 ± 1.88 |

As shown in Table 4, the administration groups 9-11, to which a composition comprising collagen peptide or L-hydroxyproline alone was administered as a sample liquid, did not show an increase in the amount of L-hydroxyproline in the skin, i.e., the total amount of soluble collagen and insoluble collagen. In contrast, the administration groups 7 and 8, to which collagen peptide and L-hydroxyproline were simultaneously administered, showed a remarkable increase in the total amount of soluble collagen and insoluble collagen.

Experimental Example 3

Healthy 11 persons (ages 25-60) were divided into two groups of a test group (6 persons) and a control group (5 persons), and subjected to a double blind ingestion test for 4 weeks. The test substance filled in two hard capsules was ingested with water every day after supper. The composition of the test substance is shown in Table 5.

TABLE 5

| | collagen peptide (mg/tablet) | L-hydroxyproline (mg/tablet) | crystalline cellulose[1] (mg/tablet) | L-alanine: L-hydroxyproline |
| --- | --- | --- | --- | --- |
| test group | 250 | 50 | 20 | 1:3.67 |
| control group | — | — | 350 | — |

[1]manufactured by ASAHI KASEI CHEMICALS CORPORATION, Ceolus FD301

After 4 weeks from the ingestion of the test substance, a questionnaire survey relating to the improvement in the dryness of the face was performed. In the control group, 40% of the test subject recognized improvement, and 83.3% of the test group recognized improvement in the condition of face. Thus, a remarkable effect was afforded by the ingestion of collagen peptide and L-hydroxyproline.

Experimental Example 4

The drinks obtained in Example 5 and Comparative Example 1 were subjected to a sensory evaluation by two persons. The drink obtained in Example 5 was evaluated as being "easy to drink", whereas the drink obtained in Comparative Example 1 was evaluated as being "a little difficult to drink due to a smell unique to collagen".

Examples of the present invention are shown in the following.

Example 1

Water-soluble collagen peptide SS (manufactured by Kyowa Hakko Kogyo Co., Ltd., 100 g) and trans-4-hydroxy-L-proline (manufactured by Kyowa Hakko Kogyo Co., Ltd., 500 g) were mixed to give an oral composition. The weight ratio of alanine and hydroxyproline contained in the amino acids obtained by hydrolyzing the oral composition was 1:58.84.

Example 2

Water-soluble collagen peptide SS (manufactured by Kyowa Hakko Kogyo Co., Ltd., 500 g) and trans-4-hydroxy-L-proline (manufactured by Kyowa Hakko Kogyo Co., Ltd., 500 g) were mixed to give an oral composition. The weight ratio of alanine and hydroxyproline contained in the amino acids obtained by hydrolyzing the oral composition was 1:12.86.

Example 3

Water-soluble collagen peptide SS (manufactured by Kyowa Hakko Kogyo Co., Ltd., 500 g) and trans-4-hydroxy-L-proline (manufactured by Kyowa Hakko Kogyo Co., Ltd., 100 g) were mixed to give an oral composition. The weight ratio of alanine and hydroxyproline contained in the amino acids obtained by hydrolyzing the oral composition was 1:3.67.

Example 4

Water-soluble collagen peptide SS (manufactured by Kyowa Hakko Kogyo Co., Ltd., 500 g) and trans-4-hydroxy-L-proline (manufactured by Kyowa Hakko Kogyo Co., Ltd., 300 g) were mixed to give an oral composition. The weight ratio of alanine and hydroxyproline contained in the amino acids obtained by hydrolyzing the oral composition was 1:8.26.

Example 5

The following components were dissolved in distilled water to a total amount of 100 ml, whereby a drink containing collagen and L-hydroxyproline was produced. The weight ratio of alanine and hydroxyproline contained in the amino acids obtained by hydrolyzing the oral composition was 1:3.67.

TABLE 6

| components | amount (g) |
| --- | --- |
| trans-4-hydroxy-L-proline | 0.4 |
| water-soluble collagen peptide SS (Kyowa Hakko Kogyo Co., Ltd.) | 2.0 |
| High-Craft M75 (fructose content 55 wt %, manufactured by Nihon Cornstarch Corporation) | 5.45 |
| citric acid | 0.15 |

Comparative Example 1

The respective components below were dissolved in distilled water to a total amount of 100 ml, whereby a drink containing collagen was produced.

TABLE 7

| components | amount (g) |
| --- | --- |
| water-soluble collagen peptide SS (Kyowa Hakko Kogyo Co., Ltd.) | 5.0 |
| High-Craft M75 (fructose content 55 wt %, manufactured by Nihon Cornstarch Corporation) | 5.45 |
| citric acid | 0.15 |

The above-mentioned components were dissolved in distilled water to a total amount of 100 ml.

Example 6

Tablet Containing Hydroxyproline and Collagen Peptide

The respective components below are uniformly mixed, and the mixture is tableted by a single-punch tableting machine to give a tablet with a diameter of 5 mm and a weight of 15 mg.

TABLE 8

| components | amount (g) |
| --- | --- |
| trans-4-hydroxy-L-proline | 2.0 |
| collagen peptide SS (Kyowa Hakko Kogyo Co., Ltd.) | 10.0 |
| sodium ascorbate | 10.0 |
| lactose | 74.0 |
| dry Cornstarch | 2.0 |
| talc | 1.8 |
| magnesium stearate | 0.2 |

Example 7

Granules Containing Hydroxyproline and Collagen Peptide

The tablet obtained in Example 2 is pulverized, granulated and sieved to give 20-50 mesh granules.

Example 8

Drink (2) Containing Hydroxyproline and Collagen Peptide

The respective components below are uniformly dissolved by stirring and purified water is added to a total amount of 1000 ml, whereby a drink containing trans-4-hydroxy-L-proline is produced.

In the following components, q.s. for flavor and dye means an amount used for conventional production of drink, and q.s. for purified water means an amount necessary for making the total amount 1000 ml, in addition to other components.

TABLE 9

| components | amount (g) |
| --- | --- |
| trans-4-hydroxy-L-proline | 2.0 |
| collagen peptide SS (Kyowa Hakko Kogyo Co., Ltd.) | 10.0 |
| sodium ascorbate | 5.0 |
| sodium benzoate | 1.0 |
| fructose | 10.0 |
| flavor | q.s. |
| pigment | q.s. |
| purified water | q.s. |

Example 9

Candy Containing Hydroxyproline and Collagen Peptide

A candy made of the following components and containing trans-4-hydroxy-L-proline is produced according to a conventional method.

TABLE 10

| components | amount (g) |
| --- | --- |
| trans-4-hydroxy-L-proline | 2.0 |
| collagen peptide SS (Kyowa Hakko Kogyo Co., Ltd.) | 10.0 |
| sorbitol powder | 5.0 |
| flavor | 0.2 |
| sorbitol seed | 0.05 |

Example 10

Capsule Containing Hydroxyproline and Collagen Peptide

The respective components below are measured, fed into a blending machine, and sufficiently mixed to uniformity. The mixture is filled in a hard-type gelatin capsule according to a conventional method to give a hard capsule containing about 500 mg of trans-4-hydroxy-L-proline per 1 capsule.

TABLE 11

| components | amount (g) |
| --- | --- |
| trans-4-hydroxy-L-proline | 2.0 |
| collagen peptide SS (Kyowa Hakko Kogyo Co., Ltd.) | 10.0 |
| microcrystalline cellulose | 63.0 |
| colloid silicon dioxide | 12.5 |
| magnesium stearate | 12.5 |

INDUSTRIAL APPLICABILITY

The present invention can provide an oral composition comprising collagen or gelatin or a degradation product thereof, and hydroxyproline or a salt thereof, which is effective for promotion of collagen synthesis and the like.

The invention claimed is:

1. A method of promoting collagen synthesis or reducing face dryness, comprising administering to a subject in need thereof an oral composition comprising (a) a composition of collagen or gelatin or a degradation product thereof, and (b) hydroxyproline or a salt thereof,
wherein
the weight ratio of (a):(b) in the oral composition is 1:0.2-5.0,
the weight ratio of the free form of alanine to the free form of hydroxyproline obtained by hydrolyzing the oral composition is 1:3.5-60,
the weight of hydroxyproline liberated by hydrolysis of the oral composition is 0.1-1 g, and
the composition is in one or more discrete portions.

2. The method of claim 1, wherein the oral composition is formed by adding hydroxyproline or a salt thereof to the composition of collagen or gelatin or a degradation product thereof.

3. The method of claim 1, wherein the hydrolyzing is hydrolyzing with an acid or alkali.

4. A method of promoting collagen synthesis or reducing face dryness, comprising administering to a subject in need thereof an oral composition comprising (a) collagen or gelatin or a degradation product thereof, and (b) hydroxyproline or a salt thereof,
wherein
the weight ratio of (a):(b) in the oral composition is 1:0.2-5.0,
the weight ratio of the free form of alanine to the free form of hydroxyproline obtained by hydrolyzing the oral composition is 1:3.5-60,
the weight of hydroxyproline liberated by hydrolysis of the oral composition is 0.1-1 g, and
the composition is in one or more discrete portions.

5. The method of claim 4, wherein the oral composition is formed by adding hydroxyproline or a salt thereof to the collagen or gelatin or a degradation product thereof.

6. The method of claim 4, wherein the hydrolyzing is hydrolyzing with an acid or alkali.

* * * * *